(12) United States Patent
Wozencroft

(10) Patent No.: US 10,864,088 B2
(45) Date of Patent: Dec. 15, 2020

(54) HIP CUP ALIGNMENT GUIDE

(71) Applicant: Embody Orthopaedic Limited, London (GB)

(72) Inventor: Robert Michael Wozencroft, Central London (GB)

(73) Assignee: Embody Orthopaedic Limited, London (GB)

( * ) Notice: Subject to any disclaimer, the term of this patent is extended or adjusted under 35 U.S.C. 154(b) by 132 days.

(21) Appl. No.: 16/322,319

(22) PCT Filed: Aug. 2, 2017

(86) PCT No.: PCT/GB2017/052246
§ 371 (c)(1),
(2) Date: Jan. 31, 2019

(87) PCT Pub. No.: WO2018/025034
PCT Pub. Date: Feb. 8, 2018

(65) Prior Publication Data
US 2019/0159910 A1    May 30, 2019

(30) Foreign Application Priority Data

Aug. 2, 2016 (GB) .................................. 1613337.3

(51) Int. Cl.
*A61F 2/46* (2006.01)
*A61F 2/34* (2006.01)
*A61B 17/56* (2006.01)

(52) U.S. Cl.
CPC .............. *A61F 2/4609* (2013.01); *A61F 2/34* (2013.01); *A61B 2017/568* (2013.01); *A61F 2/4657* (2013.01); *A61F 2002/4687* (2013.01)

(58) Field of Classification Search
CPC ................................. A61F 2/4609; A61F 2/34
See application file for complete search history.

(56) References Cited

U.S. PATENT DOCUMENTS

| | | | | |
|---|---|---|---|---|
| 2001/0051830 | A1* | 12/2001 | Tuke | A61F 2/4609 623/22.12 |
| 2002/0116007 | A1* | 8/2002 | Lewis | A61F 2/4609 606/99 |
| 2004/0215200 | A1* | 10/2004 | Tornier | A61F 2/4609 606/91 |

(Continued)

FOREIGN PATENT DOCUMENTS

| | | |
|---|---|---|
| WO | WO-2012048362 A1 | 4/2012 |
| WO | WO-2018025034 A2 | 2/2018 |
| WO | WO-2018025034 A3 | 3/2018 |

OTHER PUBLICATIONS

"International Application Serial No. PCT/GB2017/052246, International Search Report dated Feb. 21, 2018", 4 pgs.

(Continued)

*Primary Examiner* — Christian A Sevilla
(74) *Attorney, Agent, or Firm* — Schwegman Lundberg & Woessner, P.A.

(57) ABSTRACT

The present invention provides a cup positioning guide which has a mechanical link from a cup introducer connection distal to the hip socket, to one or more landmarks on the pelvis. It facilitates intra-operative checks and adjustments to be made to reamed hip socket depth, cup anteversion and cup rotation with the aid of a cup trial component.

18 Claims, 10 Drawing Sheets

(56) References Cited

U.S. PATENT DOCUMENTS

Figure 1:
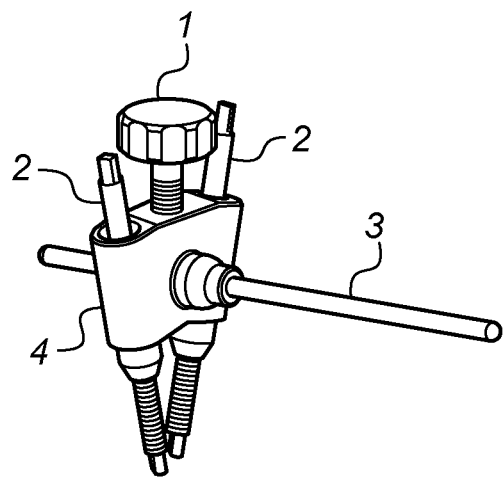

| | | | |
|---|---|---|---|
| 2005/0085823 A1* | 4/2005 | Murphy | A61F 2/4609 606/91 |
| 2005/0187562 A1* | 8/2005 | Grimm | A61F 2/4609 606/130 |
| 2005/0209604 A1* | 9/2005 | Penenberg | A61F 2/4609 606/91 |
| 2006/0184177 A1* | 8/2006 | Echeverri | A61B 17/1746 606/91 |
| 2007/0156155 A1* | 7/2007 | Parker | A61F 2/4609 606/91 |
| 2008/0051910 A1* | 2/2008 | Kammerzell | A61B 90/36 623/22.21 |
| 2008/0269757 A1 | 10/2008 | Mcminn | |
| 2014/0052149 A1* | 2/2014 | van der Walt | A61B 17/1746 606/130 |
| 2014/0094925 A1* | 4/2014 | Satterthwaite | A61F 2/4684 623/22.12 |
| 2015/0238326 A1 | 8/2015 | Satterthwaite | |

OTHER PUBLICATIONS

"International Application Serial No. PCT/GB2017/052246, Written Opinion dated Feb. 21, 2018", 7 pgs.

\* cited by examiner

HIP CUP ALIGNMENT GUIDE

This application is a U.S. National Stage Application under 35 U.S.C. 371 from International Application Serial No. PCT/GB2017/052246, filed on Aug. 2, 2017, and published as WO 2018/025034 A2 on Feb. 8, 2018, which claims priority to United Kingdom Application No. 1613337.3, filed on Aug. 2, 2016, the benefit of priority of each of which is claimed hereby, and each of which are incorporated by reference herein in its entirety.

In hip replacement surgery, the acetabular cup implant is usually orientated in the acetabulum either using the introducer shaft as a guide or by using an acetabulum alignment guide attached to the introducer. Examples of acetabulum alignment guides generally include two rods perpendicular to one another. The inclination angle of the cup is set by placing one of these rods parallel to the transverse axis of the patient and the anteversion angle is set by placing the other parallel to the longitudinal axis of the patient. However, despite all care having been taken, the orientation of the cup in the replaced hip can deviate from the ideal. This may be due to one or more factors. First the positioning of the cup is judged by aligning the introducer shaft or alignment rods by eye and as the position to be judged is a compound angle, it is difficult to visualise particularly without a guide. Second as the natural face of the acetabulum is not uniform and where the hip is arthritic may be distorted by osteophytes, the acetabulum edge is not generally a reliable guide for orientating the cup implant. A third problem is that alignment guides usually rely on the pelvis being in a known position which may itself be difficult to judge particularly with obese patients. A fourth problem is that alignment guides are usually set to fixed angles of inclination and anteversion. This is generally acceptable for the majority of patients, however in some circumstances the surgeon may wish to vary anteversion according to the natural anatomy of the patient. In view of these difficulties, the cup may sometimes be located as much as about 20 degrees from the optimum angles.

Alternatively the acetabular cup prosthesis can be orientated by computer based navigation or by using pre-manufactured patient specific instruments (PSI). Navigation has been shown to achieve accurate cup alignment, however it requires additional very complex and expensive equipment in the operating theatre. It also relies on registering the position of the pelvis intraoperatively which is difficult and time consuming to do as there is limited access to register bone surfaces within the surgical site. Patient specific instruments are also difficult to position due to the limited access to bone surfaces. Both navigation and patient specific instruments are associated with complex and time consuming pre-operative planning and additional costs. Furthermore they do not guarantee correct cup alignment if the registration operation (or in the case of PSI the positioning operation) fails or is inaccurate.

During computer based planning of hip replacement operations it is common to identify the anterior pelvic plane (APP) for reference. The APP connects the anterior superior iliac spines (ASIS's) and the pubic symphysis. The ASIS's are easily palpated (identified by feel through the skin) and are often used by the surgeon to judge position of the pelvis on the operating table whether or not computer based planning and navigation is used. The axis between ASIS's is also a useful datum for cup inclination. The pubic symphysis is less easily palpated because the depth of soft tissue varies too much between patients.

To address these difficulties, the present invention provides a cup positioning guide which has a mechanical link from a cup introducer connection distal to the hip socket, to one or more landmarks on the pelvis. It facilitates intraoperative checks and adjustments to be made to reamed hip socket depth, cup anteversion and cup rotation with the aid of a cup trial component. Furthermore because cup introducer connection is distal to the hip socket and detachable, the cup trial can be exchanged for the cup implant leaving the guide fixed in position. Therefore the guide directs the final cup implant to exactly the same position and orientation as the cup trial. The present invention cup positioning guide can be either generic or patient specific.

In some arrangements, particularly in e.g. a patient specific guide, the guide will preferably have a fixed inclination angle, fixed anteversion angle (without anteversion adjustment) and possibly (but not essentially) including axial rotation adjustment. In other arrangements, such as in e.g. a generic guide, the guide will preferably have a fixed inclination, variable anteversion and possibly (but not essentially) including axial rotation adjustment.

It is desirable to protect those features apart from the axial rotation for both patient specific and generic (since most acetabular cups do not have rotational features, therefore they do not need axial adjustments).

The skilled person will appreciate that in the guides described herein, there can be a variety of combinations of the various parts that can be moveable. Thus, in some guides one might have means to adjust the inclination angle, the anteversion angle and provide for adjustable axial rotation. In some arrangements of the guide described herein, there can be adjustable inclination angles but e.g. fixed anteversion and no means for axial rotation. Alternatively there might be an adjustable or fixed inclination angle, an adjustable or fixed anteversion angle, and an adjustable or no means to adjust the axial rotation.

In some arrangements of the guide of the present invention, the guide preferably has at least two important features: a connection hub being the hub that provides the connection of the guide to the first anchor which will typically be (fixed) on the body; and the guide extending away from the body to a distal region where the surgeon can connect and manipulate the introducer. The distal region is typically positioned a distance away from the connection hub so as to allow the introducer to be suitably positioned and manipulated without compromising the accuracy of the use of the guide and introducer. Typically the guide can be arranged such that an introducer attached to the connector is directed towards the proximal region of the guide and, when in use, into the socket of a hip.

Thus, there is provided a cup positioning guide comprising a proximal region (which broadly can be considered as being preferably the whole region of the guide that is closest to the hip (i.e. the first ASIS connector and the second ischium connector)) and a distal region (which broadly is preferably where the introducer connector is located), said proximal region comprising a connection hub to connect to at least a first landmark anchor (such as e.g. an ASIS marker) and said distal region comprising at least a connector for a cup introducer, said connection hub and said connector being linked by a mechanical linkage.

The mechanical linkage provides a scaffold which in use allows the surgeon to be reasonably confident that an introducer (with a cup implant attached to it) can be accurately positioned so as to achieve a best fit for the cup implant into e.g. the hip of a patient.

In preferred arrangements, the guide also comprises a second anchor which is connected to the main body of the guide. The connection hub and second anchor are therefore mechanically linked. The body of the guide provides a rigid linkage between these two features. The distance/orientation between these two features can in some arrangements of the guide be adjusted, for example depending on the size of the patient. These two features combine with the first anchor which preferably is on or connected to the body (as will be the second anchor when the guide is in use) to provide for a stable scaffold of the main body of the guide, on which the connector for the introducer is associated and can be accurately aligned to the hip socket.

Thus, there is provided a cup positioning guide wherein the proximal region of the cup positioning guide further comprises at least a second landmark anchor, said second landmark anchor being positioned away from said connection hub and said second landmark anchor being connected to said mechanical linkage linking said connection hub and said connector.

Preferably the second landmark anchor comprises an anchor for connecting to an ischium corner.

Preferably the mechanical linkage comprises a main body portion linking said connection hub and said second landmark anchor. The second landmark anchor will typically extend from the main body of the guide back towards the patient (when in use). In some arrangements, the second landmark anchor will be at the end of an arm extending from the main body.

In other arrangements, of the cup positioning guide the mechanical linkage preferably comprises an arm extending from the main body to the distal region, said arm comprising a connector for a cup introducer at the distal region.

Preferably the connector at the distal region is arranged such that there is provided an inclination angle Y between an axis of said connector extending from said connector to said proximal region and an axis running through said connection hub. The inclination angle is described in more detail below.

In some arrangements, the inclination angle is fixed. In other arrangements, the guide is arranged to comprise means which can be used to vary the inclination angle. This can provide for accurate positioning of the cup implant.

In some arrangements, the connector at said distal region is arranged such that there is provided an anteversion angle Z between an axis of said connector extending from said connector to said proximal region and an axis running through said second landmark anchor. The anteversion angle is described in more detail below.

In some arrangements (such as in patient specific guides) the arm is immovable in respect of said main body. In such arrangements, the anteversion angle will have been manufactured into the guide based on profiles of the patient typically taken prior to surgery.

Alternatively, the arm can be fixedly moveable in respect of said main body. The skilled person will be aware of a number of arrangements as to how this can be achieved. In one arrangement, the main body can comprise an arced section and said arm is fixedly moveable on said arced section in order to adjust an anteversion angle Z. This can be by means of a rail arrangement, as described herein.

In addition to any of the various features described herein, the connector for a cup introducer can further comprise means to rotate the cup introducer. This can be particularly useful if the (cup) implant being used is asymmetric, such that it must be fitted into the patient in a particular orientation in order to allow it to function most efficiently.

The skilled person will be aware of a number of ways in which the cup introducer can be rotated. In one arrangement, for example, the means to rotate a cup introducer is by way of a worm drive. The cup introducer will have a complementary portion on its shaft which is able to interact with the worm drive in order to allow the introducer to be rotated.

In certain arrangements, the connection hub of the cup positioning guide can be connected to a first landmark anchor by at least one rod. This rod can be provided as part of the guide, or can be a separate piece that can be introduced to the guide in order to complete the connection.

In some arrangements, the connection hub has means to fixedly adjust the location of the at least one rod in order to provide for a means of best fit of the cup positing guide to the first landmark anchor. These means will typically be one or more holes extending into and optionally through the connection hub in order to receive the rod at different heights in respect of the main body of the guide.

In some arrangements, the connection hub can comprise a multi-articulate joint which is connectable to said first landmark anchor and which allows freedom to adjust the position of a second landmark anchor.

In use, the cup positioning guide can be associated with a hip of a patient, wherein the connector is distal to the hip socket and wherein said first landmark anchor is on the pelvis.

Preferably the first landmark anchor is for positioning on the operative side ASIS of a pelvis. Where there is a second landmark anchor, this is typically for positioning on the ischium adjacent to the hip socket. This provides for secure attachment of the guide in order to allow correct positioning of an implant into e.g. the hip.

In preferred arrangements of the cup positioning guide, where the guide comprises mechanical anteversion adjustment, the centre of rotation is coincident with the hip socket centre so that the anteversion adjustment does not shift (cup) implant position.

There is also provided a cup positioning guide having a multi-articulate joint between a first landmark anchor (e.g. ASIS marker) and a connection hub which allows freedom to position a second landmark anchor e.g. on the ischium adjacent to the hip socket whilst maintaining a constant angle between the anterior pelvic plane (APP) and the axis between ASIS and projected hip socket centre position.

Preferably, the mechanical linkage maintains a constant angle between the ASIS axis and a cup face, also known as the cup inclination angle.

In some arrangements, there is provided a cup positioning guide with connection for a cup introducer distal to the hip socket, which can be disconnected and reconnected. The cup introducer preferably also has a common connection to receive a cup trial as well as the final cup implant, so that the final cup implant is directed to exactly the same position and orientation as the cup trial.

Preferably, the cup positioning guide is single use.

The cup positioning guide can be cup size specific.

In some arrangements, the main body and/or the introducer arm of the cup positioning guide comprises a plastics material. This can be formed via additive manufacturing.

The present invention cup positioning guide uses one or preferably uses both anterior superior iliac spine (ASIS) positions as reference positions. These positions are not within the main surgical exposure, therefore they must located by palpating subcutaneously or contacted directly by making very small incisions in their respective locations. Both ASIS positions are only accessible when the patient is laying in the supine position, but during the hip replacement operation it is more common for the patient to be laid on their side supported by padded supports attached to the operating table. Therefore a pre-operative procedure is undertaken to fix a marker to the operative side ASIS. During this procedure, a bridging guide is positioned to reference both ASIS positions while the marker is fixed directly to the operative side ASIS with screw pins. The bridging guide is then removed leaving the marker fixed in position. The marker thus holds a relative axis between both ASIS positions but is only attached to one of them. The patient is then turned on their side for the hip replacement operation. This procedure is used elsewhere, particularly in computer based navigation, therefore it is known and not part of the claimed invention.

A third reference position for the guide is within the surgical site on the ischium adjacent to the hip socket. The position of the ischium is accessible and a reliable reference because it is shaped approximately as a corner, with the lateral edge forming one side and the anterior edge forming the other side of the corner. Furthermore this ischium corner is flanked by a ridge of bone at the edge of the hip socket. It is therefore possible for a corner fitting piece on the guide to locate the corner of bone and to be in contact with the hip socket edge, making it an easily identifiable and repeatable third reference position.

Figure 2:
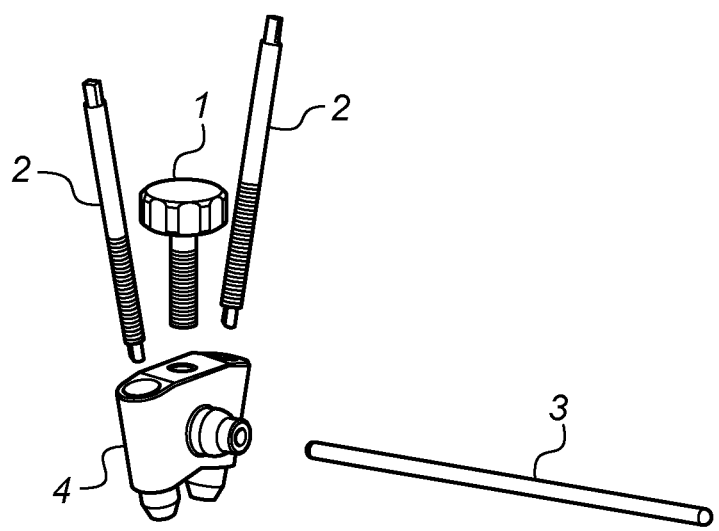
Figure 3:
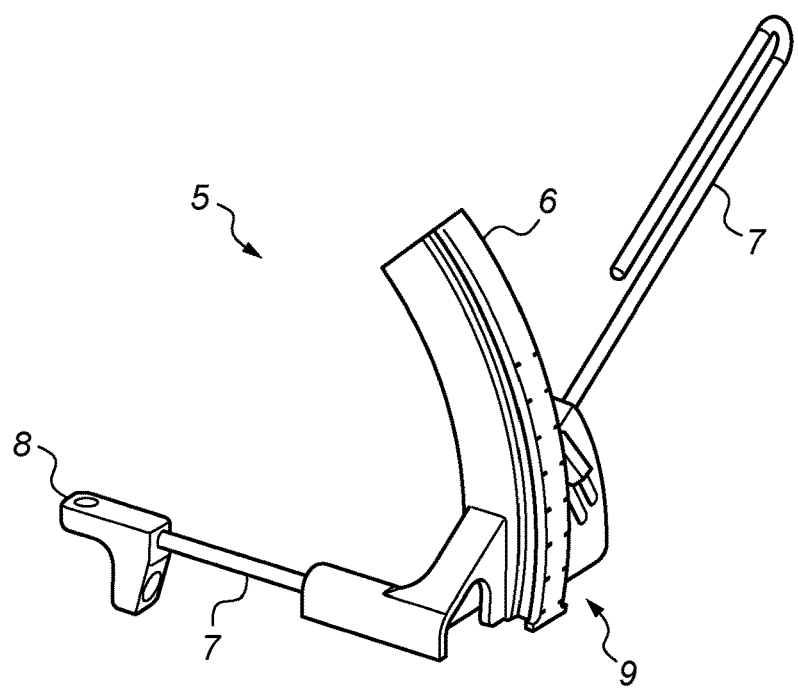
Figure 4:
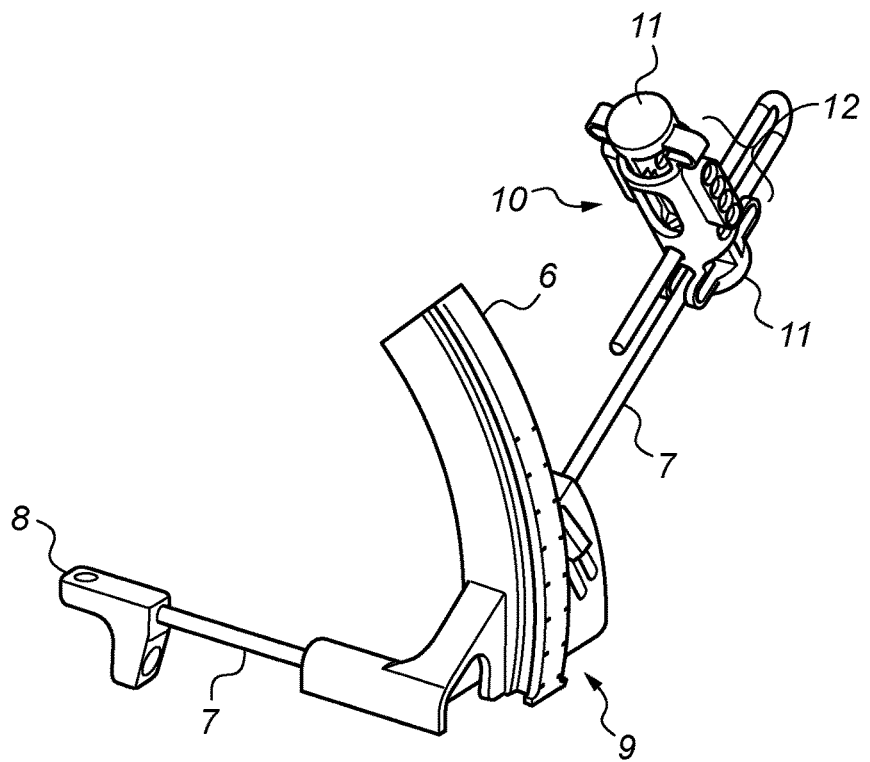
Figure 5:
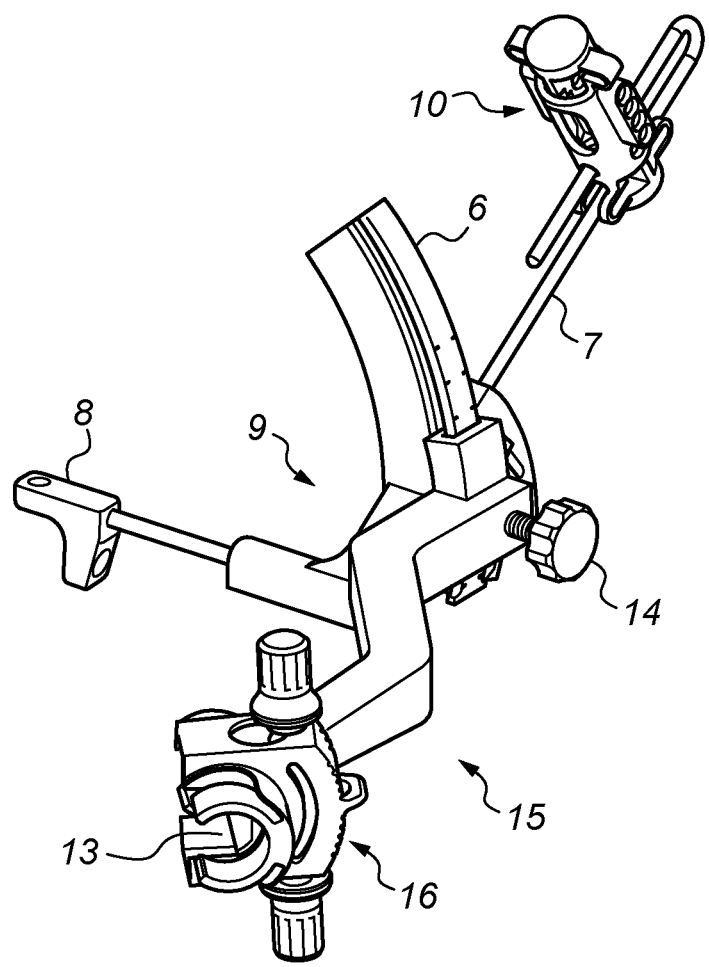
Figure 6:
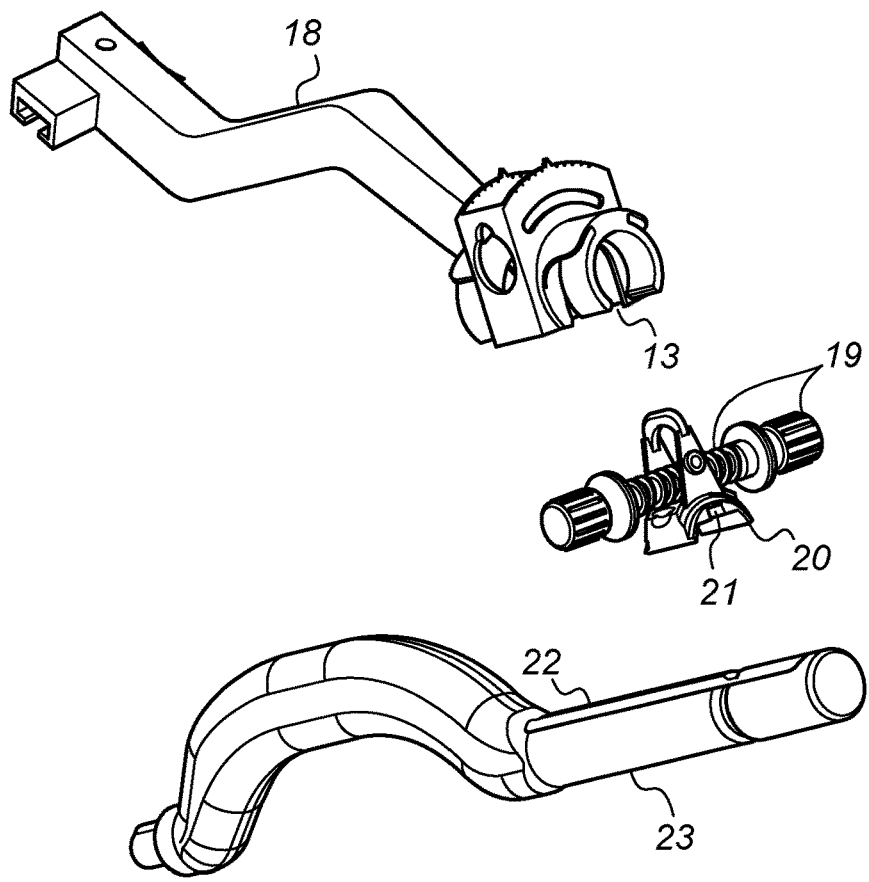
Figure 7:
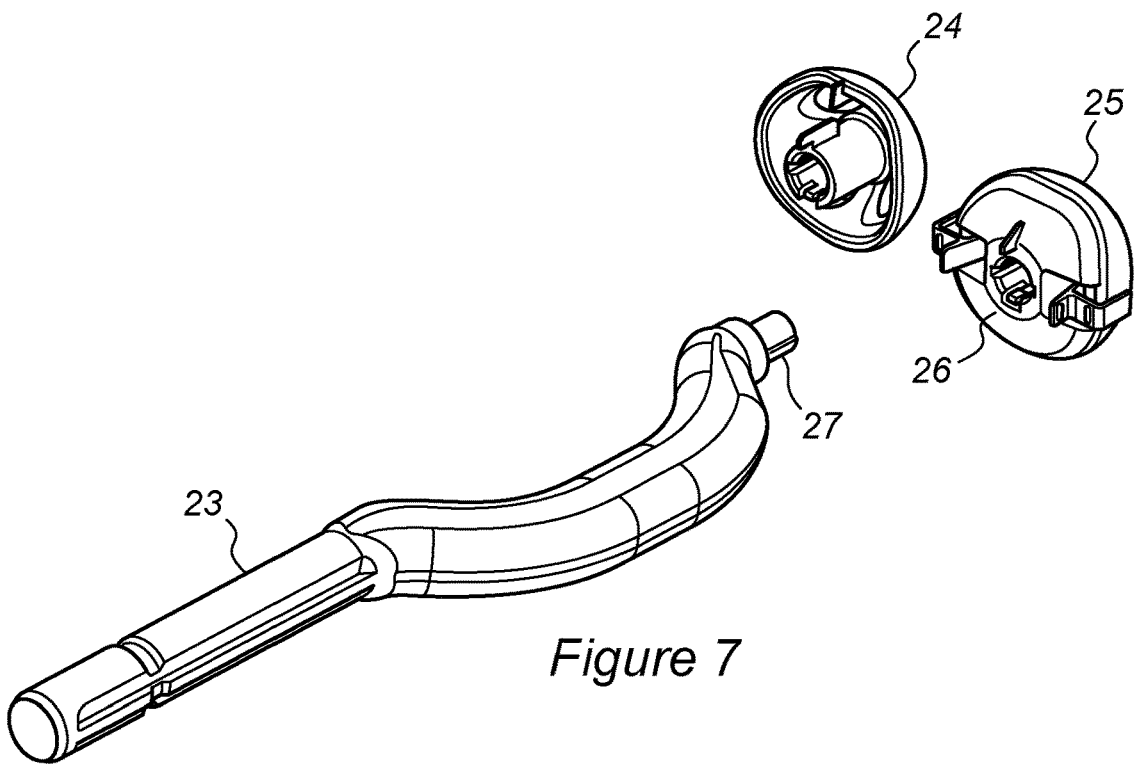
Figure 8:
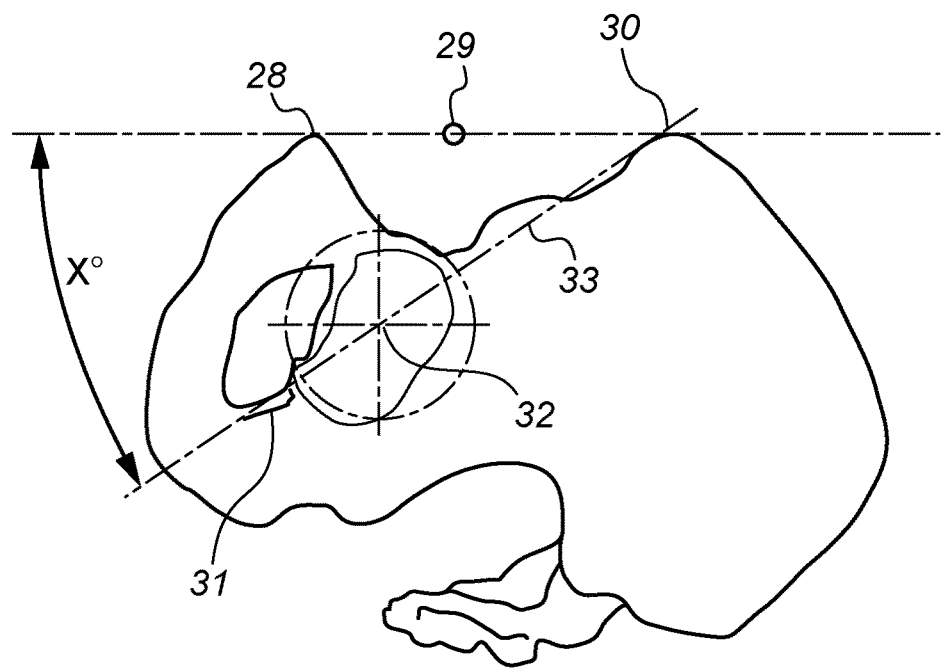
Figure 9:
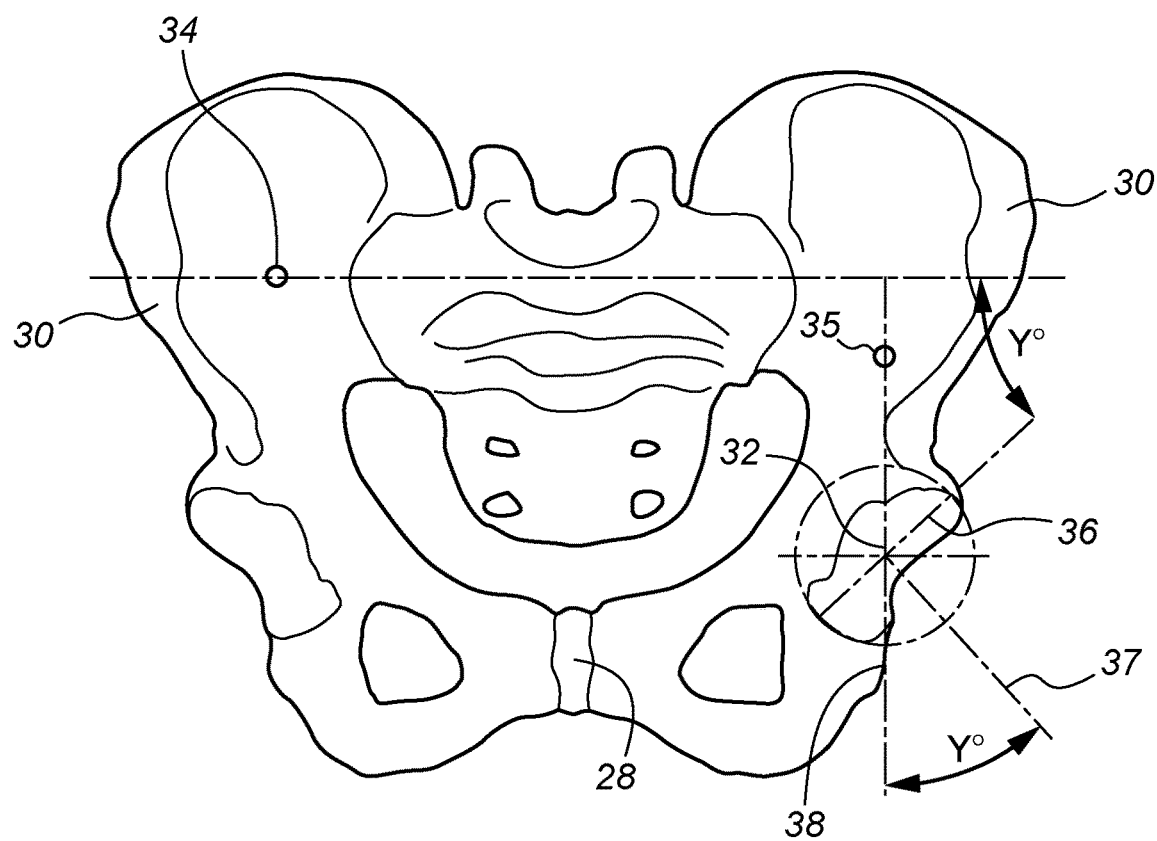
Figure 10:
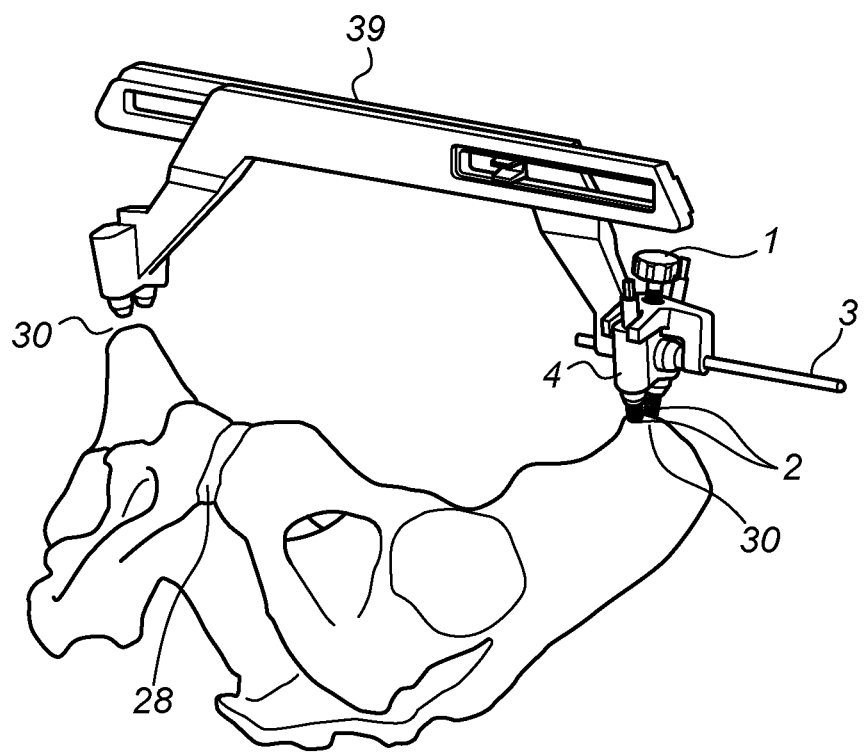
Figure 11:
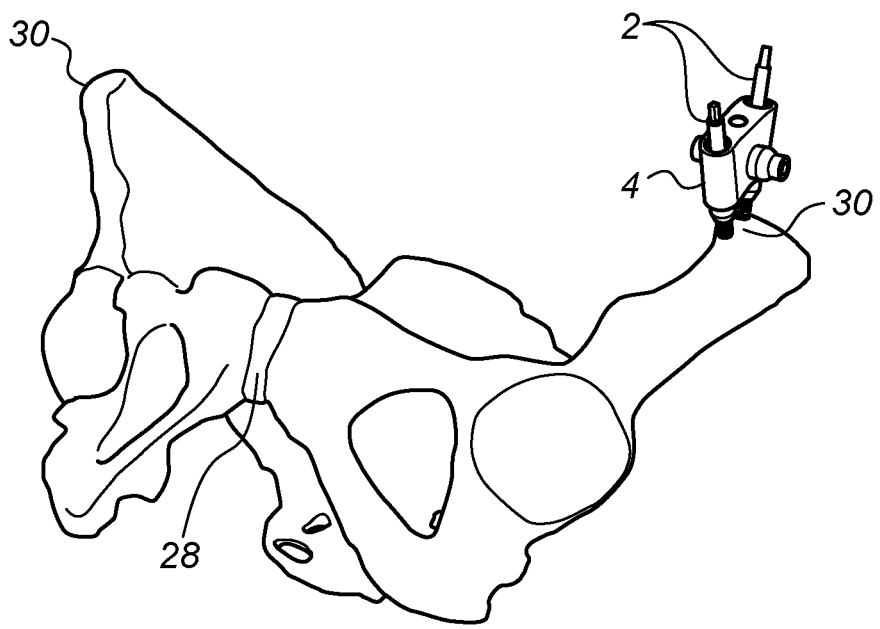
Figure 12:
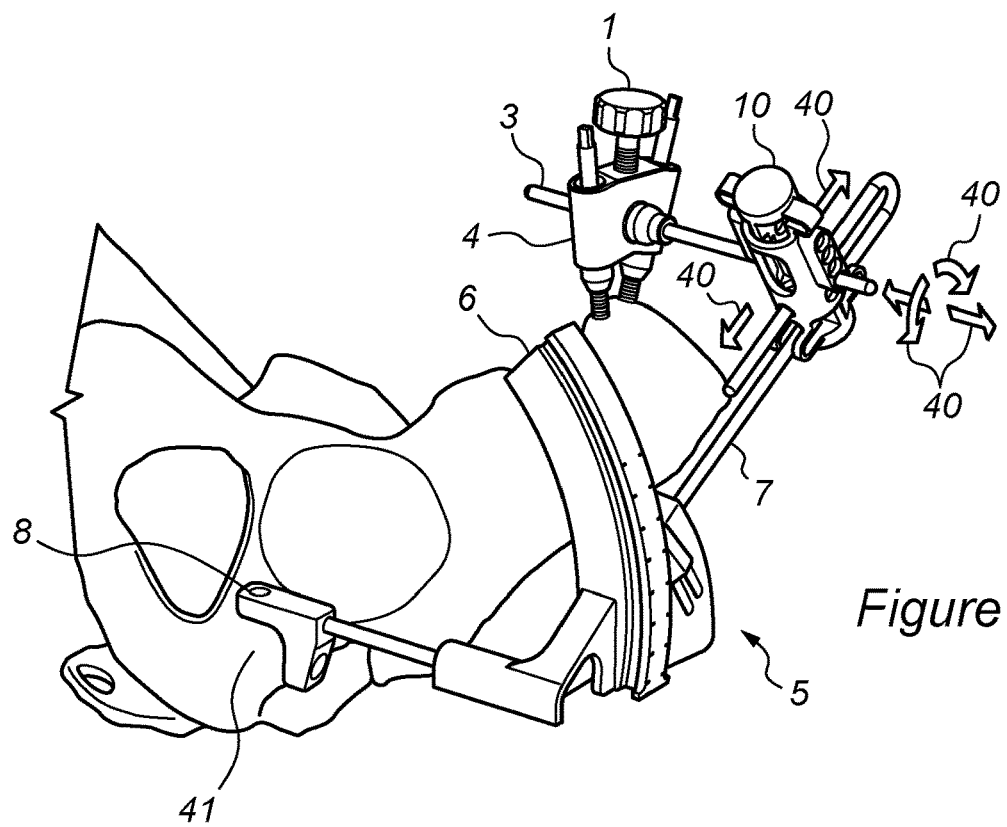
Figure 13:
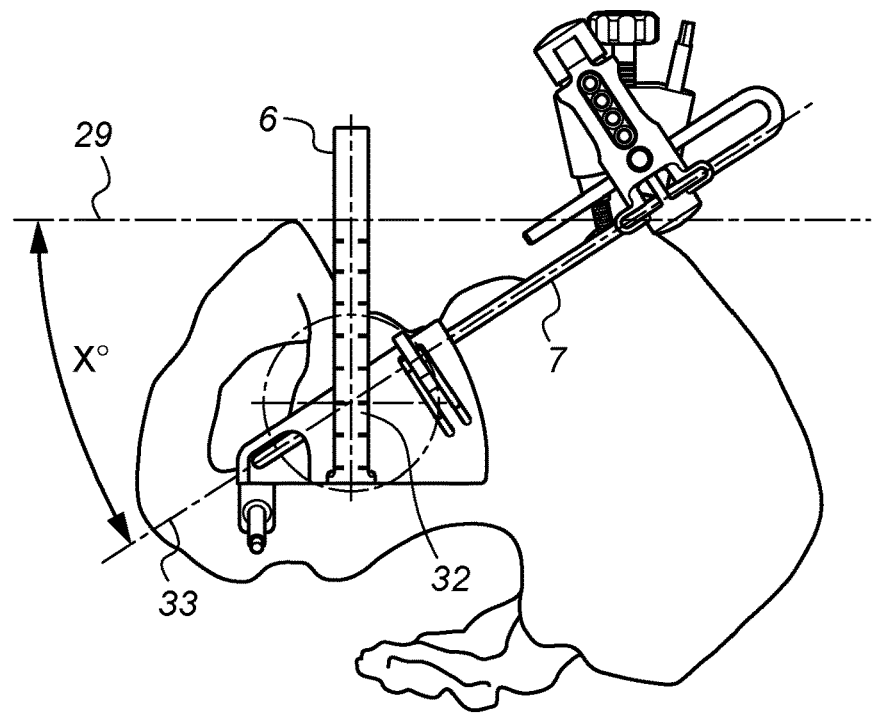
Figure 14:
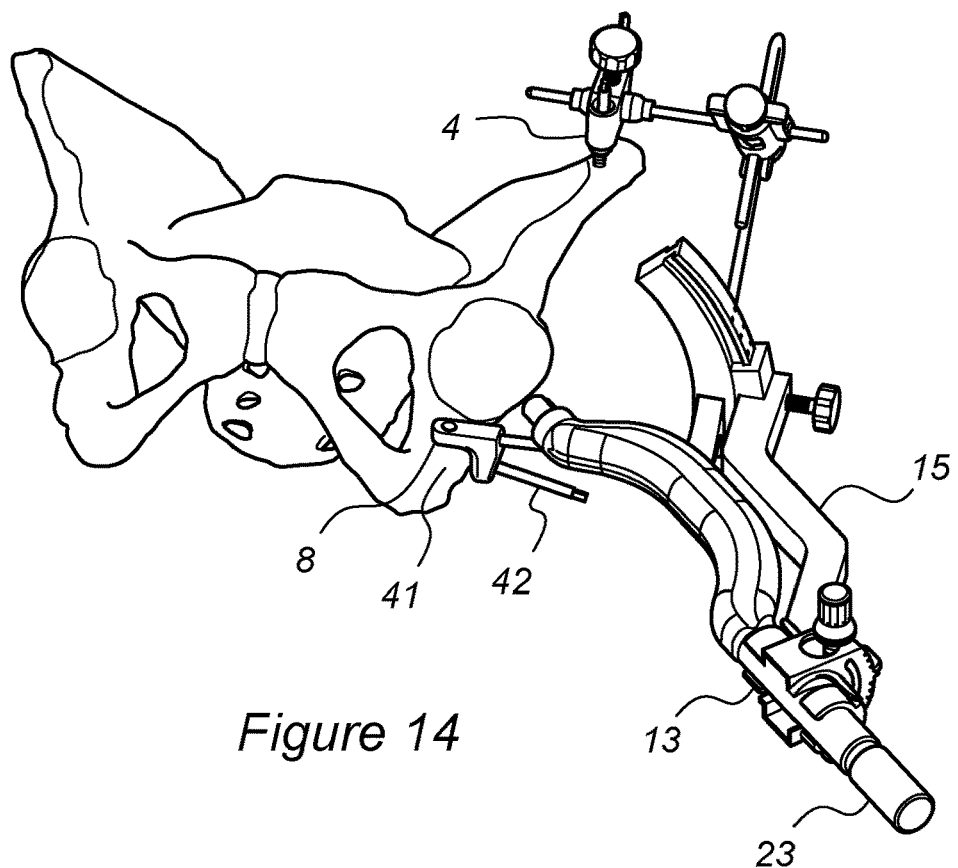
Figure 15:
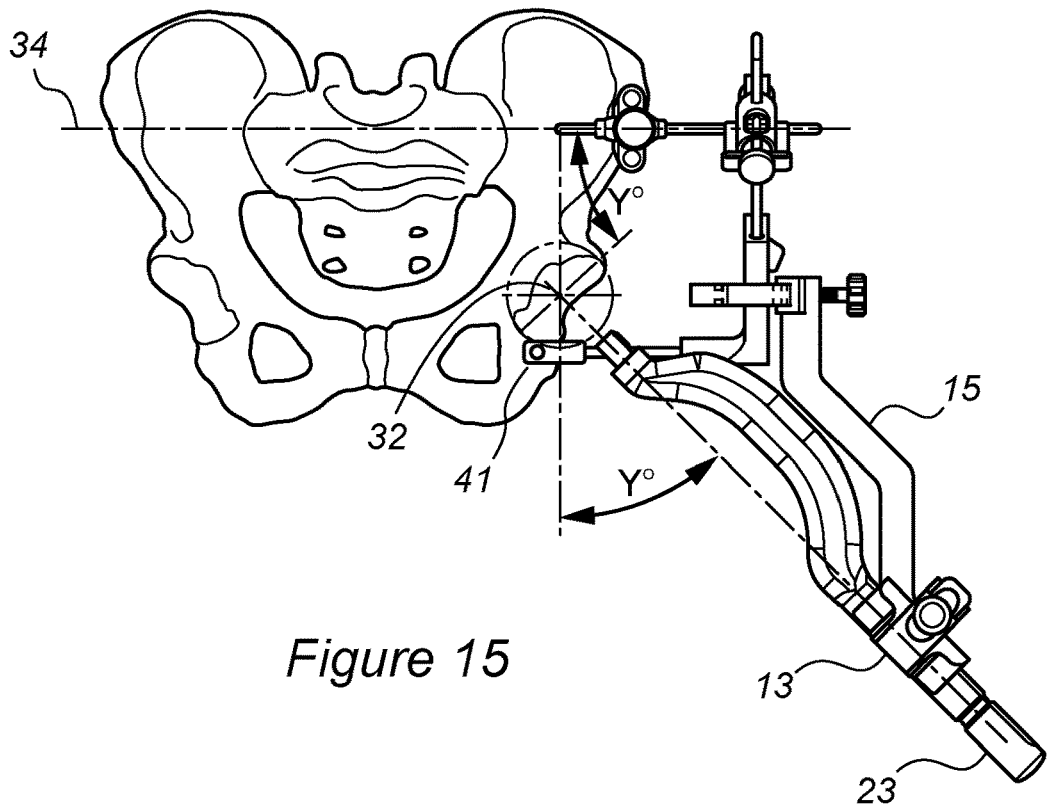
Figure 16:
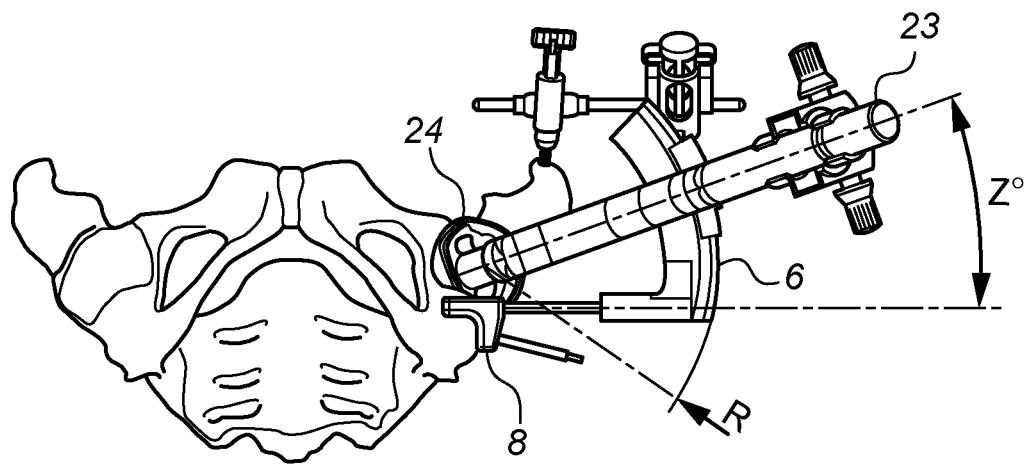
Figure 17:
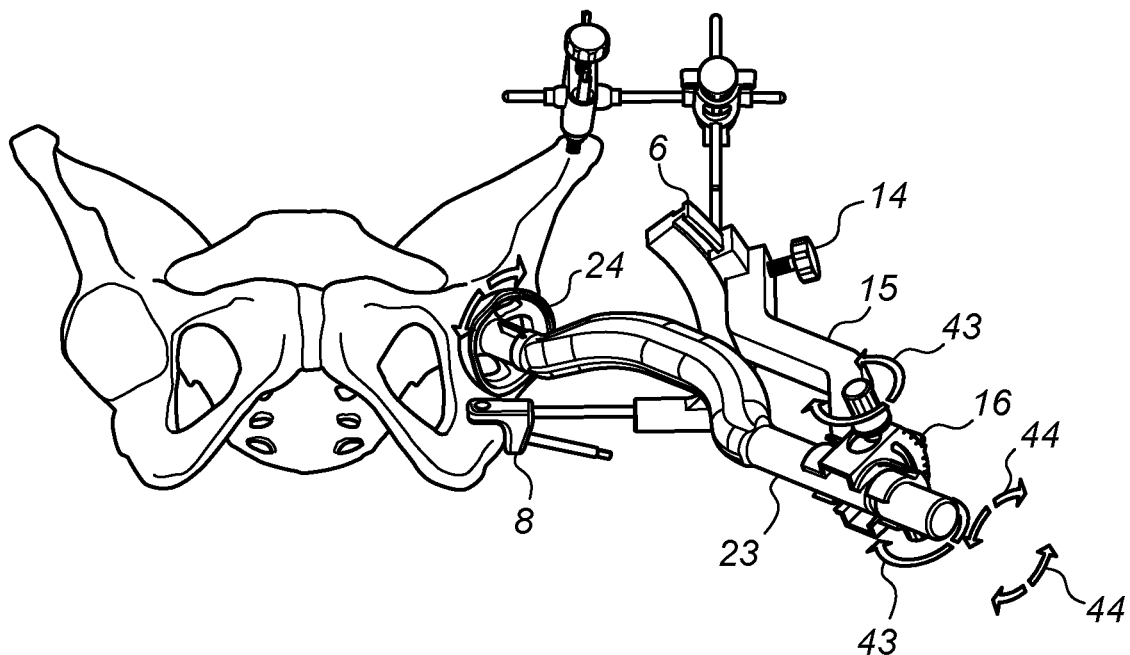
Figure 18:
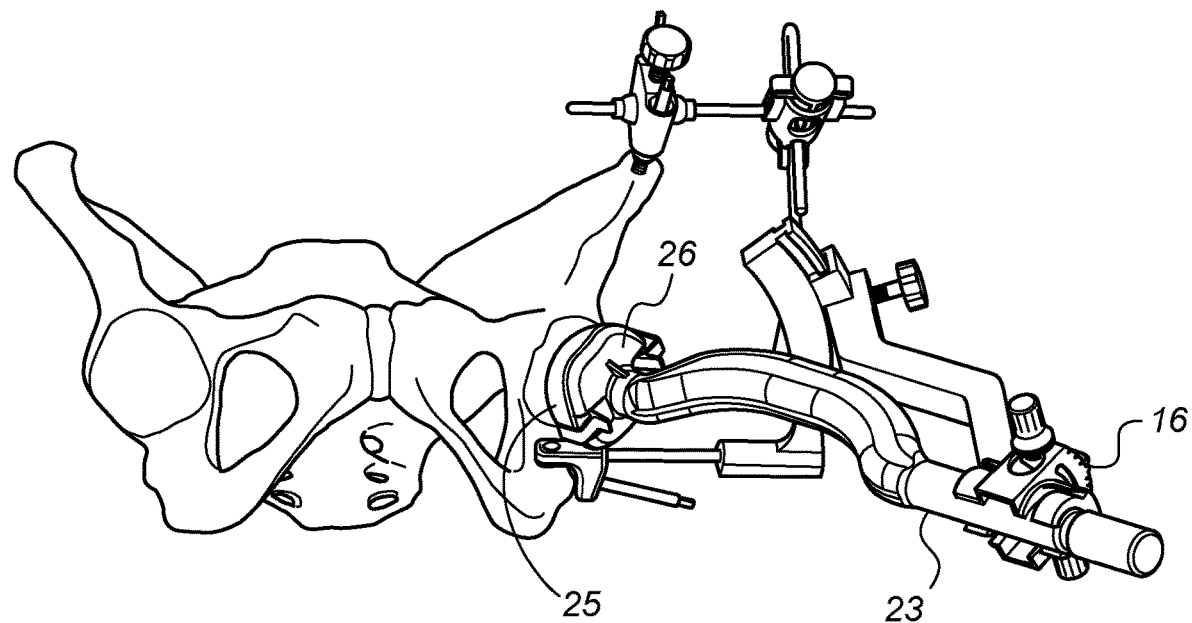
Figure 19:
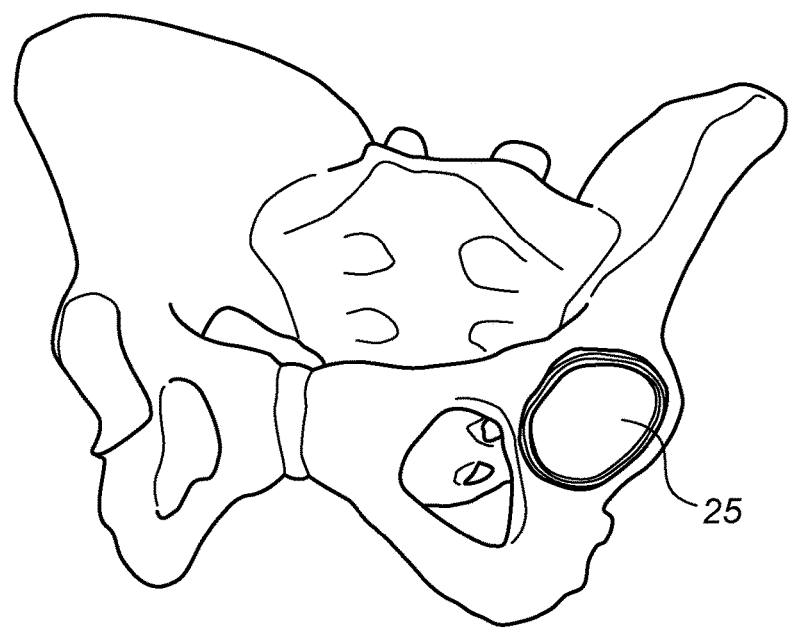

Examples of the invention will now be described by referencing the accompanying drawings:

FIG. 1 is the ASIS marker.
FIG. 2 is an exploded view of the ASIS marker.
FIG. 3 is the assembled core guide.
FIG. 4 is the core guide with a connecting hub attached.
FIG. 5 is the core guide with connecting hub and introducer arm attached.
FIG. 6 is an exploded view of the introducer arm and introducer shaft.
FIG. 7 is the introducer shaft with connection to cup trial and cup implant shown.
FIG. 8 is a lateral view of a human pelvis (with axis and hip socket centre drawn on).
FIG. 9 is a frontal view of a human pelvis (with axis and hip socket centre drawn on).
FIG. 10 is the bridging guide for mounting the ASIS marker.
FIG. 11 is the ASIS marker attached to a pelvis.
FIG. 12 is the core guide attached to the ASIS marker via the connecting hub.
FIG. 13 is a lateral view of FIG. 12.
FIG. 14 is the assembled guide with introducer arm and introducer shaft attached.
FIG. 15 is a frontal view of FIG. 14 (with axis and hip socket centre drawn on).
FIG. 16 is a view of the assembled guide in the transverse anatomical plane with introducer shaft and cup trial attached (with axis and hip socket centre drawn on).
FIG. 17 is a view of the assembled guide with introducer shaft and cup trial attached (with arrows showing adjustment).
FIG. 18 is a view of the assembled guide where the cup trial has been exchanged for the cup implant.
FIG. 19 is the cup implant implanted in the hip socket.

THE DIFFERENT PARTS OF THE CUP POSITIONING GUIDE WILL BE DESCRIBED WITH REFERENCE TO FIGS. 1-7

The ASIS marker is shown in FIGS. 1 and 2, consisting of a central part [4], straight rod [3], thumb screw [1] and two screw pins [2]. The central part and thumb screw are preferably manufactured in plastic (for example nylon) and the rod and screw pins are manufactured in metal (for example stainless steel).

The assembled core guide [5] is shown in FIG. 3, consisting of a shaped rod [7] (bent into a profiled shape), a main part [9] and a corner marker [8]. FIG. 4 has the additional connecting hub [10] attached which connects the guide to the ASIS marker via the straight rod [3]. The shaped rod [7] has a portion bent back on itself which prevents rotation of the shaped rod in the connecting hub. The connecting hub has a simple mechanism which grips the rods, however this grip is released by pressing the buttons [11] at each end towards each other (for example between thumb and forefinger) and then both rods are able to slide freely in the hub. This provides sliding adjustment between the rods ([3] and [7]) and the hub [10] when needed.

The hub also has several holes [12] for inserting the straight rod [3] from ASIS marker at different heights. This is to adjust for varying thicknesses of skin layer above the ASIS's. If the skin layer is very thin the straight rod is inserted into the hole closest to the shaped rod. However with a thicker skin layer, it's inserted into one of the subsequent holes (there are e.g. approx. 4 mm increments between each hole). Skin layer thickness is a judgement the surgeon is able to make through palpation. It is only necessary if the ASIS markers are positioned over the skin. If the markers are placed through very small incisions and therefore in direct contact with ASIS, no adjustment is necessary and the straight rod is inserted into the hole closest to the shaped rod. Alternatively a connecting hub with only two perpendicular holes is provided for this second scenario (not shown). The main part [9], corner piece [8] and connecting hub [10] are preferably manufactured in plastic (for example nylon) and the shaped rod [7] is manufactured in metal (for example stainless steel).

The introducer arm [15] has been added in FIG. 5, which articulates on the arced section [6] of the core guide and is held in position by thumb screw [14]. The introducer arm incorporates a connection [13] for the introducer shaft [23] and a worm drive [16]. In FIG. 6 the two part worm drive (worm [19] and worm-gear [20]) are shown together with the introducer arm main body [18] and introducer shaft [23]. When assembled the worm drive rotates the introducer shaft about its long axis by engaging a slot on the worm-gear [21] with a web [22] on the introducer shaft [23].

The introducer shaft [23] is shown together with cup trial [24] and cup implant [25] in FIG. 7. The cup implant incorporates a protective cap [26]. It can be seen that the cup trial [24] and cup implant protective cap [26] have identical locating features to assemble them in rotational position on the introducer shaft spigot [27]. There are separate rotational positions for left and right hips which are marked clearly, but these are not visible in the diagrams. The introducer arm [15], cup trial [24] and protective cap [26] are preferably manufactured in plastic (for example nylon) and the introducer shaft [23] is manufactured in metal (for example aluminium alloy).

The Anatomical Reference Positions Will Now be Described with Reference to FIGS. 8 and 9

The anterior pelvic plane (APP) [29] connecting the anterior superior iliac spines (ASIS's) [30] and the pubic symphysis [28] is shown in FIG. 8 (lateral view of the pelvis). An axis [33] is drawn from the ASIS position through the centre of the hip socket [32]. Angle 'X' is the angle between the APP [29] and axis [33]. Also shown is the anterior edge [31] of the corner of the ischium adjacent to the socket edge. It can be seen that this anterior edge of the ischium approximately coincides but is slightly below axis [33]. It will be illustrated later that a feature of the cup positioning guide takes up axis [33] at angle 'X'. Anatomical studies suggest that although the distances between these landmark positions vary significantly with size, angle 'X' is fairly consistent between human subjects of all sizes. One option therefore is to provide a generic cup positioning guide where angle X is set to an average value which is approximately correct for most patients. A second option would be to provide a generic guide for females and a generic guide for males if the variance from average can be reduced by doing so. A third option is that angle 'X' could be derived from preoperative scans for a particular patient and used to manufacture a patient specific cup positioning guide with unique angle 'X' and ischium position.

The axis [34] between contralateral ASIS's is shown in FIG. 9. This axis is generally accepted as the preferred datum for cup inclination rather than the longitudinal body axis because the pelvis may be tilted when the patient is laid on their side. Axis [35] is perpendicular to axis [34] and coincides with the hip socket centre [32]. Angle 'Y' is the inclination angle of the cup implant, it can either be measured from axis [34] to the cup face [36], or from axis [35] to the cup axis [37]. This angle should be within prescribed limits (known as the safe zone) is usually specified by the manufacturer for a particular cup implant to ensure optimum performance of the hip replacement device. It is normally between 35 and 45 degrees depending on implant type. For the purposes of the cup positioning guide it will be a fixed angle (not adjustable). Also shown in FIG. 9 is the lateral edge [38] of the corner of the ischium adjacent to the socket edge. It can be seen that this lateral edge of the ischium [38] approximately coincides with axis [35]. It will be illustrated later that a feature of the cup positioning guide takes up fixed angle 'Y'.

The Procedure for Using the Cup Positioning Guide Will Now be Explained with Reference to FIGS. 10-19

A pre-operative procedure is undertaken to fix a marker to the operative side ASIS. The bridging guide [39] is positioned to reference both ASIS positions [30] while the ASIS marker [4] is fixed directly to the operative side ASIS with screw pins pi as shown in FIG. 10. The bridging guide [39] is then removed leaving the ASIS marker [4] fixed in position (see FIG. 11). The marker thus holds a relative axis between both ASIS positions but is only attached to one of them. Most commonly the patient is turned on their side for the hip replacement operation (posterior approach). This procedure of fixing an ASIS marker to one side is used elsewhere, particularly in computer based navigation, therefore it is known and not part of the claimed invention. Alternatively another operative approach to the hip may be used (for example the anterior approach) where both ASIS's are more accessible during the operation so one or two ASIS markers can be attached intraoperatively, or it may not be necessary to fix ASIS markers if the bridging guide is held in position against the skin by a surgical assistant.

The hip socket is prepared with hemispherical reamers to the correct size beforehand. As most cup implants are a jam fit, the socket is normally prepared slightly undersized (one or two millimetres smaller than cup size).

In FIG. 12, the core guide [5] is linked to the ASIS marker [4] via the straight rod [3] and hub connector [10]. The arrows [40] indicate the multi-articulate joint between the ASIS marker and the core guide. These three degrees of freedom allow pivoting of the core guide approximately about the ASIS axis [34] and translational movements in two perpendicular directions, enabling the corner marker [8] to be positioned on the ischium corner [41] within the main surgical site. None of these movements alter the angle (angle 'X') between the APP plane [29] and axis [33] between ASIS and projected hip socket centre position [32] as illustrated in FIG. 13. It can also be seen in FIG. 13 that the arced portion [6] of the core guide is positioned in the centre of the projected hip socket [32].

For the generic version of the cup positioning guide the core guide is preferably cup size specific, with one for each cup implant size. Assumptions must be made to determine angle 'X' but also the theoretical position of the hip socket centre relative to the ischium corner [41] so that the axis of the introducer shaft is directed to the socket centre position. Anatomical studies suggest that angle 'X' does not vary significantly between human subjects, whereas the hip socket centre relative to the ischium corner varies according to socket size (radius). It is therefore advantageous to have sized specific core guides (one for each cup implant size) so that socket radius variable can be set into the guide without the need for a further size adjustment. Furthermore the average position of the ischium corner relative to socket centre can be set into the size specific guide.

For the patient specific version of the core guide all of these measurements can be determined precisely in a pre-operative plan and set into the guide without any assumptions. Furthermore the corner marker [8] can be manufactured to fit the exact contours of the ischium bone surface for a particular patient so it has a more precise engagement.

In FIG. 14, a third screw pin [42] has been added to fix the corner marker on the ischium. The introducer arm [15] and introducer shaft [23] have been added and it is obvious that the introducer shaft axis is approximately coincident with the hip socket centre. In FIG. 15 (frontal view) it can be seen that a fixed inclination angle (angle 'Y') is set into the guide.

In FIG. 16, a cup trial [24] has been added which is a close fit in the pre-prepared hip socket. The cup trial is slightly smaller than the cup implant (which must be a tight jam fit) so that the trial inserts fully into the socket and moves around without being tight. The centre of the arced portion of the guide [6] is coincident with the hip socket centre (as indicated by the letter 'R') so that as the introducer arm is swept through an arc to adjust variable angle 'Z', the cup trial remains in the socket centre. Angle 'Z' is the cup anteversion angle and it is helpful for the surgeon to adjust this angle and at the same time visualise how the cup edge fits in relation to the socket edge. Anteversion angle 'Z' is locked by a thumb-screw [14].

Those knowledgeable in the art of hip replacement surgery will appreciate that anteversion can be defined in three ways, anatomical anteversion, operative anteversion or radiographic anteversion and all three are slightly different because they have different spatial arrangements. In this embodiment of the cup positioning guide, the anteversion adjustment is set-up for anatomic anteversion, therefore the axis of rotational adjustment is parallel to the longitudinal body axis. However in an alternative embodiment it can be set up for operative anteversion where the axis of rotational adjustment is parallel to the transverse anatomical axis (a movement akin to hip flexion). Or in another alternative embodiment it can be set up for radiographic anteversion.

All three have in common that the axis of rotation are coincident with the hip socket centre so that the anteversion adjustment does not shift cup position.

It is also apparent in FIG. 17 that a further adjustment to cup axial rotation can be made via the worm drive [16] on the introducer arm [15], as indicated by arrows 43 and 44). This is only required if the cup has rotational features such as fins or contours (intended to be orientated in specific anatomical positions). The worm drive rotates the introducer shaft about the shafts long axis by engaging with a web feature on the shaft [22]. Those familiar with the worm drive mechanism will appreciate that it provides fine adjustment (a gross turn of the worm only results in a slight turn of the worm-gear) and it cannot be back driven by turning the worm gear via its slotted engagement with the introducer shaft. Therefore once adjusted, it reliably holds its set-to position.

Also at this stage it is easy for the surgeon to visualise and make an assessment of whether reamed socket depth is adequate. If the cup edge overhangs the hip socket edge, it may be necessary to increase the socket depth by additional reaming. This can be done with guide in position by unclipping the introducer shaft and removing the introducer arm. Following an adjustment to reamed socket depth, anteversion and cup axial rotation are re-assessed.

Once the adjustments to cup anteversion, cup axial rotation (and if necessary socket depth) have been made with the cup trial [24], the introducer shaft [23] is unclipped from its distal attachment position [13] leaving the assembled guide fixed in position. All adjustments made via the trial are set into the guide, so that when the cup trial is replaced with the cup implant [25] and the introducer shaft re-attached, the guide directs the final cup implant to exactly the same position and orientation as the cup trial.

FIG. 18 shows the introducer shaft [23] with cup implant [25] attached being directed into its final position and FIG. 19 shows it implanted in the hip socket with the cup positioning guide removed.

In the alternative embodiment patient specific cup positioning guide, it is not essential to have anteversion adjustment because pre-planned anteversion angle may be set into the guide. Furthermore it is not essential to have cup axial rotation adjustment because pre-planned axial rotation angle may also be set into the guide. However because reaming of the hip socket is done freehand (without mechanical guidance) socket position can shift slightly during reaming and it's not always possible to pre-plan how well the cup will fit in relation to the reamed socket edge. In consideration of this it may still be desirable to retain cup axial rotation adjustment with a patient specific guide.

Also due to the freehand reaming of the hip socket and/or slight migration of the socket due to the onset of arthritis, it is not always possible to predict the exact position of reamed socket. However this is not a concern for the cup positioning guide, as, due to the connection position for a cup introducer being distal to the hip socket (for example 250 mm from the socket) a small deviation in hip socket position does not make a big difference to the angles set by the guide. For example, if the socket position was shifted by 5 mm in any direction this would only equate to a 1.15 degree error from planned inclination angle. By trigonometry (tan $\Theta$=5/250, therefore $\Theta$=1.15'). Furthermore the distal connection is designed to have slight flexibility which allows the cup to find and self-centre in the reamed socket.

The invention claimed is:

1. A cup positioning guide comprising a proximal region and a distal region, said proximal region comprising a connection hub to connect to at last a first landmark anchor and said distal region comprising at last a connector for a cup introducer, said connection hub and said connector being linked by a mechanical linkage, wherein said connector for a cup introducer further comprises means to rotate a cup introducer, wherein said means to rotate a cup introducer is by way of a worm drive.

2. A cup positioning guide of claim 1, wherein said proximal region of said cup positioning guide further comprising at least a second landmark anchor, said second landmark anchor being positioned away from said connection hub and said second landmark anchor being connected to said mechanical linkage linking said connection hub and said connector.

3. A cup positioning guide of claim 2, wherein said second landmark anchor comprises an anchor for connecting to an ischium corner.

4. A cup positioning guide of claim 2, wherein said mechanical linkage comprises a main body linking said connection hub and said second landmark anchor.

5. A cup positioning guide of claim 4, wherein said mechanical linkage comprises an arm extending from said main body to the distal region, said arm comprising said connector for a cup introducer at the distal region.

6. A cup positioning guide of claim 1, wherein said connector at said distal region is arranged such that there is provided an inclination angle Y between an axis of said connector extending from said connector to said proximal region and an axis running through said connection hub.

7. A cup positioning guide of claim 6, wherein said inclination angle is fixed.

8. A cup positioning guide of claim 2, wherein said connector at said distal region is arranged such that there is provided an anteversion angle Z between an axis of said connector extending from said connector to said proximal region and an axis running through said second landmark anchor.

9. A cup positioning guide of claim 5, wherein said arm is immovable in respect of said main body.

10. A cup positioning guide of claim 5, wherein said arm is fixedly moveable in respect of said main body, wherein the main body comprises an arced section and said arm is fixedly moveable on said arced section in order to adjust an anteversion angle Z.

11. A cup positioning guide of 1, wherein said connection hub is connectable to said first landmark anchor by at last one rod.

12. A cup positioning guide of claim 11, wherein said connection hub has means to fixedly adjust the location of the at last one rod in order to provide for a means of best fit of the cup positioning guide to the first landmark anchor.

13. A cup positioning guide of claim 1, wherein said connection hub comprises a multi-articulate joint connectable to said first landmark anchor which allows freedom to adjust the position of a second landmark anchor.

14. A cup positioning guide of claim 1, wherein the connector is configured to be positioned distal to A hip socket and wherein said first landmark anchor is configured to be positioned on a pelvis.

15. A cup positioning guide of claim 14, wherein said first landmark anchor is for positioning on an operative side ASIS of a pelvis and a second landmark anchor is for positioning on an ischium adjacent to a hip socket.

16. A cup positioning guide of claim 14, comprising mechanical anteversion adjustment with centre of rotation coincident with a hip socket centre so that the anteversion adjustment does not shift cup position.

17. A cup positioning guide of claim 14 having a multi-articulate joint between said first landmark anchor and said connection hub which allows freedom to position a second landmark anchor on an ischium adjacent to a hip socket whilst maintaining a constant angle between an anterior pelvic plane (APP) and the axis between ASIS and projected hip socket centre position.

18. A cup positioning guide of claim 15, wherein said mechanical linkage maintains a constant angle between an ASIS axis and a cup face, also known as the cup inclination angle.

\* \* \* \* \*